United States Patent [19]

Hatton et al.

[11] Patent Number: 4,505,740

[45] Date of Patent: Mar. 19, 1985

[54] HERBICIDAL 5-AMINO-4-CYANO-1-PHENYL-PYRAZOLES

[75] Inventors: Leslie R. Hatton, Chelmsford; Edgar W. Parnell, Hornchurch; David A. Roberts, Bedford, all of England

[73] Assignee: May & Baker Limited, Essex, England

[21] Appl. No.: 398,336

[22] Filed: Jul. 15, 1982

[51] Int. Cl.³ .................... A01N 43/56; C07D 231/38
[52] U.S. Cl. ........................................ 71/92; 548/362
[58] Field of Search ............................ 71/92; 548/362

[56] References Cited

U.S. PATENT DOCUMENTS 3,760,084 9/1973 Marsico, Jr. et al. ............... 424/273

FOREIGN PATENT DOCUMENTS 26034 4/1981 European Pat. Off. ................ 71/92
2070604 9/1981 United Kingdom .................... 71/92

*Primary Examiner*—Henry R. Jiles
*Assistant Examiner*—Kurt G. Briscoe

*Attorney, Agent, or Firm*—Stevens, Davis, Miller & Mosher

[57] ABSTRACT

New N-phenylpyrazole derivatives of the formula:

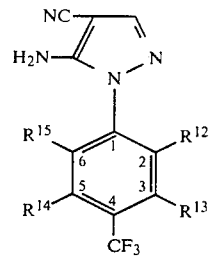

(wherein $R^{12}$ represents a chlorine atom, $R^{13}$ represents a hydrogen, fluorine or chlorine atom, $R^{14}$ represents a hydrogen or fluorine atom and $R^{15}$ represents a hydrogen, fluorine or chlorine atom, with the proviso that when $R^{14}$ represents a fluorine atom, $R^{15}$ represents a fluorine or chlorine atom, or $R^{12}$, $R^{13}$ and $R^{15}$ each represents a fluorine atom and $R^{14}$ represents a hydrogen or fluorine atom) possess useful herbicidal properties.

43 Claims, No Drawings

HERBICIDAL 5-AMINO-4-CYANO-1-PHENYL-PYRAZOLES

DESCRIPTION

This invention relates to N-phenylpyrazole derivatives, compositions containing them and their use as herbicides.

In J. Heter Chem., 12 (1975), 1199–1205, P. L. Southwick and B. Dhawan have described experiments for the preparation of 4,6-diaminopyrazolo[3,4-d]-pyrimidines in the expectation that such pyrimidine derivatives would have useful pharmacological properties. They employed as starting materials 1-phenyl-5-amino-4-cyanopyrazoles of the general formula:

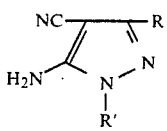

wherein R represents inter alia a hydrogen atom, and R' represents a hydrogen atom, a methyl group, a hydroxyethyl group or a phenyl group substituted by one or more chlorine atoms and/or methyl groups. Included amongst numerous pyrazole compounds prepared and disclosed by Southwick and Dhawan were 5-amino-4-cyano-1-(2,4-dichlorophenyl)pyrazole and 5-amino-4-cyano-1-(4-chloro-2-methylphenyl)pyrazole. This publication contains no suggestion that compounds of general formula I possess or would be expected to possess herbicidal activity.

Apparently these pyrazole compounds did not lead (according to the authors of the article) to useful therapeutic (viz. antimalarial) 4,6-diaminopyrazolo[3,4-d]pyrimidines.

In Japanese Patent Application 29598/63 (applied for by Takeda Chemical Industries Ltd: Publication No. 19958/65) there are disclosed pyrazole derivatives of the general formula:

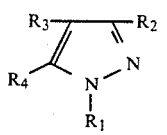

(wherein $R_1$ represents a hydrogen atom or an unsubstituted phenyl group, $R_2$ represents a hydrogen atom or a lower alkyl group, $R_3$ represents a hydrogen or halogen atom, or a nitro or cyano group and $R_4$ represents a lower alkyl group, an amino group or a lower alkoxy group) which are useful as herbicides.

Our British Patent Application No. 8105778 (British Patent Publication No. 2070604A) discloses that when the substituent $R_1$ on the pyrazole ring of compounds of general formula II is a phenyl radical carrying particular substituents, $R_2$ represents a hydrogen atom, $R_3$ represents a cyano or substituted carbamoyl radical, and $R_4$ represents an amino group, the compounds also have useful herbicidal activity and have unexpectedly advantageous herbicidal properties in relation to particular compounds disclosed in Japanese Patent Application 29598/63 (Publication No. 19958/65–Derwent Basic No. G 3904), e.g. the closely related compound 1-phenyl-4-cyano-5-aminopyrazole.

British Patent Application No. 8105778 accordingly provides, as herbicides, N-phenylpyrazole derivatives of the general formula:

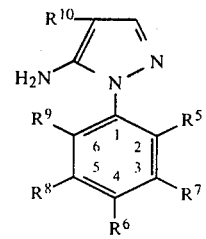

wherein each of the symbols $R^5$ and $R^6$, which may be the same or different, represents an alkyl or alkoxy radical containing from 1 to 4 carbon atoms, a trifluoromethyl, trifluoromethoxy, nitro, cyano or primary amino radical, or a fluorine, chlorine or bromine atom, each of the symbols $R^7$, $R^8$ and $R^9$, which may be the same or different, represents a hydrogen atom, an alkyl or alkoxy radical containing from 1 to 4 carbon atoms, a trifluoromethyl, trifluoromethoxy, nitro, cyano or primary amino radical or a fluorine, chlorine or bromine atom, or the symbols $R^5$, $R^7$, $R^8$ and $R^9$ each represents a hydrogen atom and the symbol $R^6$ represents a trifluoromethoxy or, preferably, a trifluoromethyl radical, and the symbol $R^{10}$ represents a cyano radical or substituted carbamoyl radical -$CONHR^{11}$ (wherein $R^{11}$ represents a methyl or ethyl radical) and, when at least one of symbols $R^5$, $R^6$, $R^7$, $R^8$ and $R^9$ represents a primary amino radical, agriculturally acceptable acid addition salts thereof.

The following compounds of general formula III are disclosed in British Patent Application No. 8105778 as being of particular interest as herbicides:

Compound

A: 5-amino-4-cyano-1-(2,3,4-trichlorophenyl)pyrazole
B: 5-amino-4-cyano-1-(2-nitro-4-trifluoromethylphenyl)pyrazole
C: 5-amino-4-cyano-1-(2,4-dichlorophenyl)pyrazole
D: 5-amino-1-(2-bromo-3,4-dichlorophenyl)-4-cyanopyrazole
E: 5-amino-4-cyano-1-(3,4-dichloro-2-methylphenyl)-pyrazole
F: 5-amino-1-(3-bromo-2,4-dichlorophenyl)-4-cyanopyrazole
G: 5-amino-4-cyano-1-(2,4-dichloro-3-methylphenyl)-pyrazole
H: 5-amino-4-cyano-1-(2,4-dichloro-3-methoxyphenyl)-pyrazole
J: 5-amino-4-cyano-1-(3-cyano-2,4-dichlorophenyl)-pyrazole
K: 5-amino-1-(4-bromo-2,3-dichlorophenyl)-4-cyanopyrazole
L: 5-amino-4-cyano-1-(2,3-dichloro-4-methylphenyl)-pyrazole
M: 5-amino-4-cyano-1-(4-bromo-2-chloro-3-methylphenyl)pyrazole
N: 5-amino-4-cyano-1-(2-chloro-3,4-dimethylphenyl)-pyrazole
P: 5-amino-4-cyano-1-(2-chloro-3-cyano-4-methylphenyl)pyrazole
Q: 5-amino-1-(3-chloro-2,4-dibromophenyl)-4-cyanopyrazole R: 5-amino-1-(3-chloro-2,4-dimethylphenyl)-4-cyanopyrazole
S: 5-amino-1-(2-bromo-4-chloro-3-methylphenyl)-4-cyanopyrazole
T: 5-amino-1-(4-chloro-2,3-dimethylphenyl)-4-cyanopyrazole
U: 5-amino-(4-chloro-3-cyano-2-methylphenyl)-4-cyanopyrazole
V: 5-amino-4-cyano-1-(2,4,5-trichlorophenyl)pyrazole
W: 5-amino-4-cyano-1-(2,4,6-trichlorophenyl)pyrazole
X: 5-amino-4-cyano-1-(2,3,4,5-tetrachlorophenyl)pyrazole
Y: 5-amino-4-cyano-1-(2,3,4,6-tetrafluorophenyl)pyrazole
Z: 5-amino-4-cyano-1-pentachlorophenylpyrazole
AA: 5-amino-4-cyano-1-pentafluorophenylpyrazole
BB: 5-amino-4-cyano-1-(4-trifluoromethylphenyl)pyrazole
CC: 5-amino-4-cyano-1-(3-chloro-2,4-difluorophenyl)pyrazole
DD: 5-amino-4-N-methylcarbonamido-1-(2,3,4-trichlorophenyl)pyrazole
EE: 5-amino-4-N-ethylcarbonamido-1-(2,3,4-trichlorophenyl)pyrazole The letters of the alphabet A to H, J to N and P to EE are assigned to the above compounds for identification and easy reference hereafter in the present specification.

Particularly preferred compounds according to British Patent Application No. 8105778 are, referring to the identification by letters of the alphabet indicated above, Compound C, and more especially Compounds D to H, J to N and P to U and, in particular, Compound A.

European Patent Application No. 0 026 034 also discloses that Compound W [5-amino-4-cyano-1-(2,4,6-trichlorophenyl)pyrazole] possesses valuable herbicidal properties.

As a result of further extensive research and experimentation, it has now been found that when the substituent $R_1$ on the pyrazole ring of compounds of general formula II is a phenyl group substituted in the 4-position by a trifluoromethyl group, in the 2-position by a chlorine or fluorine atom, and optionally in the 3-, 5- and 6-positions by fluorine or chlorine atoms as hereinafter more particularly described, these compounds unexpectedly possess outstandingly advantageous herbicidal activity in comparison with the herbicidal N-phenylpyrazole derivatives disclosed in British Patent Application No. 8105778 and other closely related compounds disclosed in the prior art.

The present invention accordingly provides, as herbicides, the new N-phenylpyrazole derivatives of the general formula:

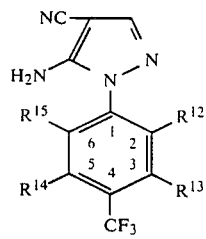

IV wherein $R^{12}$ represents a chlorine atom, $R^{13}$ represents a hydrogen, fluorine or chlorine atom, $R^{14}$ represents a hydrogen or fluorine atom and $R^{15}$ represents a hydrogen, fluorine or chlorine atom, with the proviso that when $R^{14}$ represents a fluorine atom, $R^{15}$ represents a fluorine or chlorine atom, or $R^{12}$, $R^{13}$ and $R^{15}$ each represent a fluorine atom and $R^{14}$ represents a hydrogen or fluorine atom. When $R^{13}$ represents a hydrogen atom, $R^{14}$ preferably represents a hydrogen atom.

Representative compounds of general formula IV according to the present invention include 5-amino-1-(2-chloro-4-trifluoromethphenyl)-4-cyanopyrazole (identified hereinafter as Compound No. 1), 5-amino-4-cyano-1-(2,6-dichloro-4-trifluoromethylphenyl)-pyrazole (identified hereinafter as Compound No. 2), 5-amino-4-cyano-1-(2,3,6-trichloro-4-trifluoromethylphenyl)pyrazole (identified hereinafter as Compound No. 3) and 5-amino-4-cyano1-(2,3,5,6-tetrafluoro-4-trifluoromethylphenyl)pyrazole (identified hereinafter as Compound No. 4).

In experiments on herbicidal activity carried out on representative compounds of general formula III disclosed in British Patent Application No. 8105778, the closely related compound 1-phenyl-4-cyano-5-aminopyrazole specifically disclosed in Japanese Patent Application No. 29598/1963 (test Compound CC1) and the closely related compound 5-amino-4-cyano-1-(2,3,4-trichlorophenyl)-3-methylpyrazole (test Compound CC2), and representative compounds of general formula IV (Compounds Nos. 1, 2, 3 and 4), the following results have been obtained:

EXPERIMENT 1

TEST METHODS (1) Weed Control Test
(a) General

The test compounds A to H, J to N and P to EE, CC1, CC2, No. 1, No. 2, No. 3 and No. 4 (as hereinbefore identified) were dissolved in acetone. Application was from a standard laboratory herbicide sprayer using a flat fan jet travelling at 1.6 m.p.h. (2.6 km/hour) and delivering the equivalent of 530 liters of spray fluid per hectare, the spray pressure being 2.81 kg/cm² (40 pounds/inch²). The solutions of test compounds A to H, J, K, M, N and Q to EE, CC1 and CC2 were prepared by dissolving 0.513 g of test compound in acetone and making up with more acetone to 34 ml (1.5% w/v), equivalent to an application rate of 8 kg of test compound per hectare. Solutions equivalent to 4, 2, 1, 0.5, 0.25 and 0.125 kilogrammes per hectare (kg/ha) were prepared from these solutions by serial dilution with acetone, except for test compounds C, W, AA, BB, DD, EE and CC1 for which solutions equivalent to 8, 4, 2, 1 and 0.5 kg/ha were prepared. The solutions of test compounds L and P were similarly prepared but using 0.128 g of test compound to give solutions equivalent to application rates of 2, 1, 0.5, 0.25 and 0.125 kg/ha. The solutions of test compounds Nos. 1, 2 and 4 were similarly prepared but using 0.128 g of test compound to give solutions equivalent to application rates of 2, 1, 0.5, 0.25, 0.125, 0.0625, 0.0312 and 0.0156 kg/ha. The solutions of test compound No. 3 were similarly prepared but using 0.064 g of test compound to give solutions equivalent to application rates of 1, 0.5, 0.25, 0.125, 0.0625, 0.0312 and 0.0156 kg/ha.

(b) Weed Control: Pre-emergence application

Weed seeds were sown on the surface of John Innes No. 1 potting compost (7 parts by volume of sterilized loam, 3 parts by volume of peat and 2 parts by volume of fine grit) in 9 cm diameter bitumenised paper pots. The quantities of seeds per pot were as follows:

| Weed species | Approximate number Seeds/pot |
|---|---|
| (i) Broad leafed weeds | |
| Sinapis arvensis | 30-40 |
| Polygonum lapathifolium | 30-40 |
| Stellaria media | 30-40 |
| (ii) Grass weeds | |
| Avena fatua | 15-20 |
| Alopecurus myosuroides | 30-40 |
| Echinochloa crus-galli | 20-30 |

The test compounds were applied to the uncovered seeds as described in (1) (a) above at dose rates of 0.125 to 8 kg/ha, except for test compounds L and P, which were applied at dose rates of 0.125 to 2 kg/ha, for test compounds C, W, AA, BB, DD, EE and CCl which were applied at dose rates of 0.5 to 8 kg/ha, for test compounds Nos. 1, 2 and 4 which were applied at dose rates of 0.0156 to 2 kg/ha, and test compound No. 3 which was applied at dose rates of 0.0156 to 1 kg/ha, and the seeds were covered with 25 ml of sharp sand after spraying. A single pot of each weed species was allocated to each treatment, with unsprayed controls and controls sprayed with acetone alone. After treatment, the pots were kept in the greenhouse and were treated overhead. Visual assessment of weed control activity was made 19 to 28 days after spraying. The results were expressed as the minimum effective dose (MED) in kg/ha which gave 90% reduction in growth or kill of the weeds in comparison with plants in the control pots. The results obtained are presented below in Table I.

(c) Weed Control: Post-emergence application

Weed species were grown and then transplanted at the seedling stage into John Innes No. 1 potting compost in 9 cm diameter bituminised paper pots, except for *Avena fatua*, which was sown directly in the test pot and not transplanted. The plants were then grown in the greenhouse until ready for spraying with the test compounds. The number of plants per pot and the growth stage of the plant at spraying were as follows:

| Weed species | Number of plants/pot | Growth stages at spraying |
|---|---|---|
| (i) Broad leafed weeds | | |
| Polygonum lapathifolium | 5 | 1-1½ pairs of leaves |
| Stellaria media | 5 | 4-6 leaves |
| Abutilon theophrasti | 3 | 2 pairs of leaves |
| (ii) Grass weeds | | |
| Avena fatua | 10 | 1 leaf |
| Alopecurus myosuroides | 5 | 1½ leaves |
| Echinochloa crus-galli | 5 | 1-2 leaves |

The test compounds were applied to the plants as described in (1) (a) above at dose rates of from 0.125 to 8 kg/ha, except for test compounds L and P which were applied at dose rates of 0.125 to 2 kg/ha, for test compounds C, W, AA, BB, DD, EE and CCl which were applied at dose rates of 0.5 to 8 kg/ha, for test compounds Nos. 1, 2 and 4 which were applied at dose rates of 0.0156 to 2 kg/ha, and test compound No. 3 which was applied at dose rates of 0.0156 to 1 kg/ha. A single pot of each weed species was allocated to each treatment, with unsprayed controls and controls sprayed with acetone alone. After spraying, the pots were watered overhead, commencing 24 hours after spraying. Assessment of the control of the growth of the weeds was made 19-28 days after spraying by recording the number of plants which had been killed and the reduction in growth. The results were expressed as the minimum effective dose (MED) in kg/ha which gave 90% reduction in growth or kill of the weeds in comparison with the plants in the control pots. The results obtained are presented below in Table II.

KEY TO WEED SPECIES (a) Grass Weeds:

Am = *Alopecurus myosuroides*
Af = *Avena fatua*
Ec = *Echinochloa crus-galli*

(b) Broad-Leaf Weeds

Sm = *Stellaria media*
Pl = *Polygonum lapathifolium*
Sa = *Sinapis arvensis*
At = *Abutilon theophrasti*

TABLE I

| Test Compound | PRE-EMERGENCE MED (kg/ha) | | | | | |
|---|---|---|---|---|---|---|
| | Pl | Sa | Sm | Am | Af | Ec |
| A | 0.25 | 0.125 | 0.5-1 | 0.5 | 0.5-1 | 0.125-0.25 |
| B | 0.5-1 | 0.5 | >8 | 2 | 2-4 | 1-2 |
| C | 0.5-1 | 0.5-1 | 8 | 4 | 4 | 1 |
| D | 0.5-1 | 0.25-0.5 | 4-8 | 2 | 4 | 1 |
| E | 1 | 1-2 | 2-4 | 2-4 | 2-4 | 0.5-1 |
| F | 0.5-1 | 0.5-1 | 2 | 2-4 | 1-2 | 0.5-1 |
| G | 0.25-0.5 | 0.25-0.5 | 0.5 | 1-2 | 1-2 | 0.25-0.5 |
| H | 0.5-1 | 2 | 1 | 2 | 1-2 | 2 |
| J | 0.5 | 0.5-1 | 4-8 | 2 | 1-2 | 1 |
| K | 1 | 0.5 | 1-2 | 2-4 | 2-4 | 1 |
| L | 0.5 | 1 | >>2 | >2 | >2 | 1-2 |
| M | 1 | 0.5-1 | >8 | 4 | 4 | 0.5-1 |
| N | 0.125-0.25 | 0.25 | 8 | 4 | 2-4 | 0.25-0.5 |
| P | 1 | >>2 | NR | NR | NR | 2 |
| Q | 4 | 4 | 4 | 4-8 | 4-8 | 4-8 |
| R | 1-2 | 4-8 | >8 | 2-4 | 2-4 | 1-2 |
| S | 1-2 | 0.5-1 | 2-4 | 4 | 4 | 4 |
| T | 0.5-1 | 2-4 | 4-8 | 0.5-1 | 2-4 | 2-4 |
| U | 2 | 4-8 | 4-8 | 2-4 | >8 | 2 |
| V | 1 | 2 | 8 | 8 | 4-8 | 1 |
| W | 0.5-1 | <0.5 | 2 | 2-4 | 0.5-1 | 0.5-1 |
| X | 2 | 1-2 | 0.5 | 2-4 | 2-4 | 2 |
| Y | 0.5 | 1.0 | 4-8 | 2-4 | 2 | 0.5-1 |
| Z | 2-4 | 1-2 | >>8 | 2-4 | 4-8 | 1 |
| AA | 1-2 | 1.0 | 8 | 2-4 | 1-2 | 1 |
| BB | 1-2 | 4 | 4-8 | 2-4 | 4 | 1-2 |
| CC | 1 | 4 | >>8 | 4 | 4 | 1 |
| DD | 4 | 1 | 8 | >>8 | NR | >8 |
| EE | NR | 2-4 | NR | NR | NR | >>8 |
| CCl | 8 | >>8 | 8 | NR | NR | >>8 |
| CC2 | NR | NR | NR | NR | NR | NR |
| No 1 | 0.0312-0.0625 | 0.0312-0.0625 | 0.5-1 | 0.25-0.5 | 0.25 | 0.25 |
| No 2 | 0.0156-0.0312 | <0.0156 | 0.0625-0.125 | 0.25-0.5 | 0.25-0.5 | 0.125 |
| No 3 | 0.125-0.25 | 0.0156-0.0312 | 0.0625 | 1.0 | 0.25-0.5 | 0.5 |
| No 4 | 0.0156-0.0312 | 0.0156 | 0.25 | 0.5 | 0.0312-0.0625 | 0.125 |

TABLE II

| Test Compound | POST-EMERGENCE MED (kg/ha) | | | | | |
|---|---|---|---|---|---|---|
| | At | Pl | Sm | Am | Af | Ec |
| A | 0.125 | 0.125 | 1-2 | 4-8 | 4-8 | 2-4 |
| B | 0.125 | 0.5 | >8 | >>8 | >8 | 8 |
| C | <0.5 | <0.5 | >>8 | >8 | >8 | 4 |

TABLE II-continued

| Test Com-pound | POST-EMERGENCE MED (kg/ha) | | | | | |
|---|---|---|---|---|---|---|
| | At | Pl | Sm | Am | Af | Ec |
| D | 0.125–0.25 | 0.125–0.25 | 2–4 | >8 | >>8 | >8 |
| E | <0.125 | <0.125 | 2 | >>8 | >8 | 8 |
| F | 0.125–0.25 | 0.25–0.5 | 0.5–1 | NR | >>8 | >8 |
| G | <0.125 | 0.25–0.5 | 4–8 | >>8 | >8 | 4 |
| H | 0.25 | 0.125–0.25 | 0.25 | >8 | 8 | 1–2 |
| J | <0.125 | <0.125 | NR | >8 | >8 | 1–2 |
| K | 0.25–0.5 | 0.125–0.25 | 2 | NR | >8 | >8 |
| L | <0.125 | 0.25–0.5 | >2 | >>2 | >>2 | 2 |
| M | 0.125–0.25 | 0.25–0.5 | >8 | NR | >>8 | >8 |
| N | 0.125–0.25 | 0.25–0.5 | NR | >>8 | >>8 | 8 |
| P | 0.125–0.25 | 0.5–1 | >>2 | >>2 | >>2 | NR |
| Q | 0.125–0.25 | 0.25 | 4–8 | >>8 | >>8 | >>8 |
| R | 0.125–0.25 | 0.25–0.5 | NR | >>8 | >>8 | >8 |
| S | 0.125–0.25 | 0.25–0.5 | 1–2 | NR | >>8 | >8 |
| T | 0.5–1 | 0.5–1 | NR | >>8 | >8 | >8 |
| U | 1–2 | 0.5–1 | >>8 | >>8 | >>8 | >8 |
| V | 0.25–0.5 | 0.5 | >>8 | >>8 | >>8 | >8 |
| W | <0.5 | <0.5 | >>8 | >8 | 8 | 2–4 |
| X | 0.5–1 | 0.5–1 | 2 | NR | NR | >8 |
| Y | 0.125–0.25 | 0.25–0.5 | >>8 | 8 | 4–8 | 2 |
| Z | 0.5–1 | 1–2 | NR | >8 | NR | >8 |
| AA | <0.5 | <0.5 | NR | 8 | 4 | 2–4 |
| BB | 1 | 0.5–1 | NR | >>8 | >>8 | 4–8 |
| CC | 2–4 | 2 | NR | >>8 | >8 | 4 |
| DD | 1–2 | >8 | NR | NR | NR | >>8 |
| EE | 4–8 | 8 | NR | NR | NR | >>8 |
| CC1 | >>8 | >>8 | NR | >>8 | >>8 | NR |
| CC2 | NR | NR | NR | NR | >>8 | NR |
| No 1 | <0.0156 | 0.0156–0.0312 | 0.25 | >>2 | >2 | 0.5–1 |
| No 2 | <0.0156 | <0.0156 | 0.0156–<0.0312 | >2.0 | 2.0 | 0.5 |
| No 3 | 0.0156–0.0312 | 0.0312–0.0625 | 0.0625 | >>1.0 | >>1.0 | 1.0 |
| No 4 | <0.0156 | <0.0156 | 0.0625 | 2.0 | 0.5–1 | 0.125 |

The following symbols which appear in the above Tables have the following meanings:
'>>' means much greater than
'>' means greater than
'<' means less than
'NR' means no reduction at any dose rate applied

EXPERIMENT 2

Comparison of the post-emergence activity of Compounds 1, 2 and 4 with Compound A against *Galium aparine*, *Veronica persica* and *Viola arvensis*.

The weed species *Galium aparine*, *Veronica persica* and *Viola arvensis* are resistant to the phenylurea-type herbicides isoproturon and chlortoluron at the application rates of these two herbicides normally used to control the growth of broad-leafed weeds in cereal crops. The widespread use of isoproturon and chlortoluron, particularly in Western Europe, has resulted in these three weed species becoming a particularly important problem in weed control in winter cereals.

TEST METHOD

All weed species were grown in John Innes potting compost (7 parts by volume of sterilized loam, 3 parts by volume of peat and 2 parts by volume of fine grit). At the cotyledon growth-stage, the plants were pricked out into 9 cm. diameter bitumenized paper pots and subsequently grown on in these.

The number of plants per pot and the growth stage of the plants at the time of application of the test compounds was as follows.

| Weed species | Height (cm) | Number of leaves | Number of plants per pot |
|---|---|---|---|
| *Galium aparine* | 4 to 9 | 3 to 5 (whorls) | 2 |
| *Veronica persica* | 2 to 4 | 5 to 6 | 3 |
| *Viola arvensis* | 2 to 3 | 3 to 4 | 3 |

Application of the test compounds was from a standard laboratory herbicide sprayer using a flat fan jet travelling at 1.6m.p.h. (2.6 km/hour) and delivering the equivalent of 260 liters of spray fluid per hectare, the spray pressure being 2.1 kg/cm$^2$ (30 pounds/inch$^2$). The solutions of Compound Nos. 1, 2 and 4 and Compound A were prepared by dissolving 0.154 g of test compound in acetone and making up with more acetone to a volume of 40 ml, equivalent to an application rate of 1 kg of test compound per hectare. Solutions equivalent to 0.5, 0.25, 0.125, 0.0625 and 0.0312 kg/ha were prepared from these solutions by serial dilution with acetone. Three replicate pots of each weed species were allocated to each treatment, with unsprayed controls and controls sprayed with acetone alone. After spraying, the pots were maintained in the greenhouse with overhead watering, commencing 24 hours after spraying. Assessment of the control of the growth of the weeds was made 28 days after spraying by recording the number of plants which had been killed. The results for the replicates were averaged and the mean results were expressed as the dose rate of each test compound which killed 90% of the plants (ED$_{90}$ kg/ha). The results obtained are presented below in Table III.

TABLE III

| | ED$_{90}$ kg/ha (mean of 3 replicates) | | |
|---|---|---|---|
| Test Compound | *Galium aparine* | *Veronica persica* | *Viola arvensis* |
| Compound No 1 | 0.29 | 0.11 | 0.09 |
| Compound No 2 | 0.23 | 0.10 | 0.09 |
| Compound No 4 | 0.09 | 0.09 | 0.08 |
| Compound No A | 0.75 | 0.29 | 0.31 |

EXPERIMENT 3

Control of *Galium aparine* in winter wheat with Compounds Nos. 1 and 2 and Compound A.

TEST METHOD

Wettable powder formulations were prepared from:

(A)

Compound A. 50% w/w
Arylan S90. 3% w/w
Sopropon T.36. 1% w/w

Belloid TD. 5% w/w
Silica filler SAS132 (microfine silica) to 100% by weight (B)

Compound No 1. 20% w/w
Nekal BX. 10% w/w
Sodium lignosulphate. 3% w/w
Sopropon T.36. 0.5% w/w
Silica filler SAS 132 to 100% by weight (C)

Compound No 2. 20% w/w
Nekal BX. 10% w/w
Sodium lignosulphate. 3% w/w
Sopropon T.36. 0.5% w/w
Silica filler SAS 132 to 100% by weight (Arylan S90 is sodium dodecylbenzenesulphonate; Sopropon T.36 is a sodium polycarboxylate; Belloid TD is a condensate of sodium naphthalene sulphonate and formaldehyde; Neckal BX is a sodium alkyl naphthalene sulphonate).

The wettable powders were diluted with water and applied in 217.2 liters of spray fluid per hectare to 2.5×2.5 m plots containing emerged winter wheat (variety Avalon; growth stage: height 6 inches, 5 leaves unfolded, main shoot plus four tillers, pseudostem erect) and *Galium aparine (growth stage: height* 3 inches with 2 branches and 3 rosettes to height 8 inches with 7 to 8 branches), using two replicates per treatment.

The following dose rates were applied:
Compound A: 0.5, 1 and 2 kg/ha
Compound No 1: 0.125, 0.25, 0.5 and 1 kg/ha
Compound No 2: 0.125, 0.25, 0.5 and 1 kg/ha Six days after spraying, the percentage control of *Galium aparine* and percentage damage to the wheat in each treated plot was assessed visually in comparison with unsprayed control plots. The mean percentage control and damage figures for each pair of replicated plots was then calculated and the results obtained are presented in the following Table IV. (The growth stage of the wheat at the time of assessment was: height 8 inches, 6 main leaves, main shoot plus 4 tillers, first node detectable).

TABLE IV

| Test Compound | Application rate (kg/ha) | % age control of *Gallium aparine* | % age damage to winter wheat |
|---|---|---|---|
| Compound A | 0.5 | 90 | 5 |
|  | 1 | 93 | 13 |
|  | 2 | 98 | 18 |
| Compound No 1 | 0.125 | 70 | 0 |
|  | 0.25 | 83 | 0 |
|  | 0.5 | 93 | 3 |
|  | 1 | 100 | 5 |
| Compound No 2 | 0.125 | 90 | 0 |
|  | 0.25 | 95 | 0 |
|  | 0.5 | 98 | 8 |
|  | 1 | 98 | 5 |

The above experimental results clearly demonstrate the valuable herbicidal properties of the compounds of general formula IV and the surprising and unexpected superiority in herbicidal activity, more especially by post-emergence application, possessed by the compounds of general formula IV in comparison with the compounds of general formula III, for example Compounds A, B, C, V, W, X, Y, Z, AA and BB, the closely related compound 1-phenyl-4-cyano-5-aminopyrazole disclosed in Japanese Patent Application No. 29598/63 and a closely related compound 5-amino-4-cyano-1-(2,3,4-trichlorophenyl)-3-methylpyrazole in which substitution of the 3-position of the pyrazole ring by alkyl (methyl) as taught in Japanese Patent Application No. 29598/63 is combined with substitution in the 1-position of the pyrazole ring by a substituted phenyl group (2,3,4-trichlorophenyl) found to confer high herbicidal activity in the compounds of general formula III.

In particular, it is demonstrated in Experiment 1 that, by post-emergence application, Compounds Nos. 1, 2, 3 and 4 are from at least twice to more than eight times as active as Compound A in controlling the growth of the important weed *Polygonum lapathifolium*, Compounds Nos. 1, 2, 3 and 4 are at least four times to more than sixteen times as active as Compound A and from at least thirtytwo to more than sixty times as active as Compound W in controlling the growth of the important weed *Stellaria media*, Compounds Nos. 1, 2, 3 and 4 are from at least four to more than eight times as active as Compound A and Compounds Nos. 1, 3 and 4 are from at least eight to more than sixteen times as active as Compound W in controlling the growth of *Abutilon theophrasti* and Compounds Nos. 1, 2, 3 and 4 are from at least twice to more than eight times as active as Compounds A and W in controlling the growth of *Echinochloa crus-galli*. It is further demonstrated in Experiment 2 that Compound No. 1 is more than twice as active, Compound No. 2 is more than three times as active and Compound No. 4 is more than eight times as active, as Compound A in controlling the growth of *Galium aparine*, that Compounds Nos. 1, 2 and 4 are two to three times as active as Compound A in controlling the growth of *Veronica persica* and that Compounds Nos. 1, 2 and 4 are at least three times more active than Compound A in controlling the growth of *Viola arvensis*, by post-emergence application.

Experiment 3 demonstrates the high activity and selectivity of Compound No. 1 and, more especially, Compound No. 2 in controlling the growth of the very important weed species *Galium aparine* in a crop of winter wheat. Thus, Compound No. 1 is twice as active and Compound No. 2 is at least four times as active as Compound A in controlling the growth of *Gallium aparine*, while Compounds Nos. 1 and 2 are both substantially less damaging to the winter wheat than Compound A.

Accordingly, a feature of the present invention is a method for controlling the growth of weeds (i.e. undesired vegetation) at a locus which comprises applying to the locus a herbicidally effective amount of at least one N-phenylpyrazole derivative of general formula IV. For this purpose, the N-phenylpyrazole derivatives are normally used in the form of herbicidal compositions (i.e. in association with compatible diluents or carriers suitable for use in herbicidal compositions), for example as hereinafter described.

The compounds of general formula IV show herbicidal activity against dicotyledonous (i.e. broadleafed) and monocotyledonous (e.g. grass) weeds by pre- and/or, post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula IV may be used to control the growth of broad-leafed weeds, for example, *Abutilon theophrasti, Amaranthus retroflexus, Amsinckia intermedia, Anagallis arvensis, Atriplex patula, Brassica nigra, Capsella bursa-pastoris, Chenopodium album, Chrysanthemum segetum, Circium arvense, Datura stramonium, Desmodium tortuosum, Emex austrailis, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata, Polygonum spp.,* (e.g. *Polygonum lapathifolium, Polygonum aviculare, Polygonum convolvulus* and *Polygonum persicaria*), *Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium*, and grass weeds, for example, *Alopecurus myosuroides, Apera spica-venti, Agrostis stolonifera, Avena fatua, Avena ludoviciana, Brachiaria spp., Bromus sterilis, Bromus tectorum, Cenchrus spp., Cynodon dactylon, Digitaria sanquinalis, Echinochloa crus-galli, Eleusine indica, Setaria viridis* and *Sorghum halepense* and sedges, for example *Cyperus esculentus, Cyperus iria* and *Cyperus rotundus,* and *Eleocharis acicularis.*

The amounts of compounds of general formula IV applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 10 kg of active material per hectare give good results. However, it is to be understood that higher or lower application rates may be used, depending upon the particular problem of weed control encountered.

The compounds of general formula IV may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 0.05 kg and 4.0 kg, and preferably between 0.1 kg and 2.0 kg, of active material per hectare are particularly suitable. More particularly, the compounds of general formula IV may be used to control selectively the growth of broad leafed weeds, for example to control the growth of those broad leafed species hereinbefore mentioned, by pre- or, more especially, post-emergence application in a non-directional fashion, e.g. by non-directional spraying, to an area used for growing cereal crops, e.g. wheat, barley, oats, maize and rice, before or after emergence of both the crop and weeds. The compounds of general formula IV are particularly useful for controlling selectively the growth of *Galium aparine, Veronica persica, Veronica hederifolia* and *Viola arvensis,* by post-emergence application in a non-directional fashion, e.g. by non-directional spraying, to an area used for growing cereals, e.g. wheat, barley and oats, after emergences of both the crop and weeds.

For this purpose, i.e. the selective control of broad leafed weeds by pre- or post-emergence application to an area used for growing cereal crops, application rates between 0.05 and 4.0 kg, and preferably between 0.1 kg and 2.0 kg, of active material per hectare are particularly suitable.

The high herbicidal activity of the compounds of general formula IV, and more especially Compounds Nos. 1, 2 and 4, on *Galium aparine, Veronica persica* and *Viola arvensis* renders them particularly suitable for use by post-emergence application, in association with the phenylurea-type herbicides isoproturon and chlortoluron to control the growth of a wide spectrum of weed species including, in addition to the three aforementioned weed species, *Matricaria inodora, Stellaria media, Galeopsis tetrahit, Avena fatua* and *Alopecurus myosuroides,* in particular in an emerged crop of winter wheat and barley. For this purpose, application rates between 0.125 and 0.5 kg per hectare of the N-phenylpyrazole derivative(s) and application rates between 1.25 and 2.5 kg per hectare of isoproturon or chlortoluron are generally suitable.

The compounds of general formula IV may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 10.0 kg, and preferably between 1.0 kg and 4.0 kg, of active material per hectare.

The compounds of general formula IV may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directonal fashion (e.g. by directional or non-directional spraying) at application rates between 2.0 kg and 10.0 kg, and preferably between 4.0 and 10.0 kg, of active material per hectare are particularly suitable for this purpose.

When used to control the growth of weeds by pre-emergence application, the compounds of general formula IV may be incorporated into the soil in which the weeds are expected to emerge. It will be appreciated that when the compounds of general formula IV are used to control the growth of weeds by post-emergence application, i.e. by application to the aerial or exposed portions of emerged weeds, the compounds of general formula IV will also normally come into contact with the soil and may also then exercise a pre-emergence control on later-germinating weeds in the soil. Where especially prolonged weed control is required, the application of the compounds of general formula IV may be repeated if required.

According to a further feature of the present invention, there are provided compositions suitable for herbicidal use comprising one or more of the N-phenylpyrazole derivatives of general formula IV in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula IV). The term "homogeneously dispersed" is used to include compositions in which the compounds of general formula IV are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula IV.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octylphenols or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates.

Suitably, herbicidal compositions according to the present invention may comprise from 0.05% to 10% of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminium silicate, talc, calcined magnesia, kieselguhr, tricalcium phosphate, powered cork, adsorbent carbon black and clays such as kaolin and bentonite. The solid compositions (which may take the form of dusts, granules or wettable powders) are preferably prepared by grinding the compounds of general formula IV with solid diluents or by impregnating the solid diluents or carriers with solutions of the compounds of general formula IV in volatile solvents, evaporating the solvents and, if necessary, grinding the products so as to obtain powders. Granular formulations may be prepared by adsorbing the compounds of general formula IV (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agent (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compounds of general formula IV may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of one or more compounds of general formula IV, from 2 to 10% w/v of surface-active agent, from 0.1 to 5% w/v of thickener and from 15 to 87.9% by volume of water; wettable powders which comprise from 10 to 90% w/w of one or more compounds of general formula IV, from 2 to 10% w/w of surface-active agent and from 10 to 88% w/w of solid diluent or carrier; liquid water soluble concentrates which comprises from 10 to 30% w/v of one or more compounds of general formula IV, from 5 to 25% w/v of surface-active agent and from 45 to 85% by volume of water-miscible solvent, e.g. dimethylformamide; liquid emulsifiable suspension concentrates which comprise from 10 to 70% w/v of one or more compounds of general formula IV, from 5 to 15% w/v of surface-active agent, from 0.1 to 5% w/v of thickener and from 10 to 84.9% by volume of organic solvent; granules which comprise from 2 to 10% w/w of one or more compounds of general formula IV, from 0.5 to 2% w/w of surface-active agent and from 88 to 97.5% w/w of granular carrier, and emulsifiable concentrates which comprise from 0.05 to 90% w/v, and preferably from 1 to 60% w/v, of one or more compounds of general formula IV, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the compounds of general formula IV in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [α-chloro-2,6-diethyl-N-(methoxymethyl)acetanilide], asulam [methyl(4-aminobenzenesulphonyl)-carbamate], alloxydim Na [sodium salt of 2-(1-allyloxyaminobutylidene)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl)-2-aminopropionate], bromoxynil [3,5-dibromo-4-hydroxybenzonitrile], butachlor [N-(butoxymethyl)-α-chloro-2,6-diethylacetanilide], butylate [S-ethyl N,N-diisobutyl(thiocarbamate)], carbetamide [D-N-ethyl-2-(phenylcarbamoyloxy)propionamide], chlorfenprop-methyl [methyl 2-chloro-3-(4-chlorophenyl)-propionate], chloropropham [isopropyl N-(3-chlorophenyl)carbamate], chlortoluron [N'-(3-chloro-4-methyl-phenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D [2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [(±)-2-(2,4-dichlorophenoxy)propionic acid], difenzoquat [1,2-dimethyl-3,5-diphenylpyrazolium salts], dimefuron {4-[2-chloro-4-(3,3-dimethylureido)phenyl]-2-t-butyl-1,3,4-oxadiazolin-5-one}, dinitramine [$N^1$, $N^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate], flampropisopropyl [isopropyl (±)-2-(N-benzoyl-3-chloro-4-fluoroanilino)propionate], flampropmethyl [methyl (±)-2-(N-benzoyl-3-chloro-4-fluoroanilino)-propionate], fluometuron [N'-(3-trifluoromethyl-phenyl)-N,N-dimethylurea], ioxynil [4-hydroxy-3,5-diiodobenzonitrile], isoproturon [N'-(4-isopropylphenyl)-N,N-dimethylurea], linuron [N-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop [(±)-2-(4-chloro-2-methylphenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexamethylene(thiocarbamate)], oxadiazon [3-(2,4-dichloro-5-isopropoxyphenyl)-5-t-butyl-1,3,4-oxadiazolin-2-one], paraquat [1,1'-dimethyl-4,4'-bipyridylium salts], pebulate [S-propyl N-butyl-N-ethyl(thiocarbamate)], phenmedipham [3-(methoxycarbonylamino)phenyl N-(3-methylphenyl)carbamate], prometryne [4,6-bisisopropylamino-2-methylthio-1,3,5-triazine], propachlor [α-chloro-N-isopropylacetanilide], propanil [N-(3,4-dichlorophenyl)-propionamide], propham [isopropyl N-phenylcarbamate], pyrazone [5-amino-4-chloro-2-phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], tri-allate [S-2,3,3-trichloroallyl N,N-diisopropyl(thiocarbamate)]and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butyl-carbamoyl-benzimidazol-2-yl)carbamate, 1,2-bis-(3-methoxycarbonyl-2-thioureido)benzene, isopropyl 1-carbamoyl-3-(3,5-dichlorophenyl)-hydantoin and 1-(4-chloro-phenoxy)-3,3-dimethyl-1-(2,3,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, manganese, cobalt and copper.

Herbicidal compositions according to the present invention which comprise the compounds of general formula IV, and more especially Compounds Nos. 1, 2 and 4 in association with, and preferably homogeneously dispersed in, isoproturon and chlortoluron and, if desired, one or more compatible pesticidally acceptable diluents or carriers, surface-active agents and conventional adjuvants, more especially in the ratio 1:2.5 to 1:20 by weight of N-phenyl-pyrazole derivative(s) to isoproturon or chlortoluron, are particularly suitable for use by post-emergence application to control the growth of Galium aparine, Veronica persica, Veronica hederifolia, Viola arvensis, Matricaria inodora, Stellaria media, Galeopsis tetrahit, Avena fatua and Alopecurus myosuroides, in particular in an emerged crop of winter wheat and barley.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the N-phenyl-pyrazole derivatives of general formula IV or, as is preferred, a herbicidal composition as hereinbefore described, and preferably a herbicidal concentrate which must be diluted before use, comprising at least one of the N-phenylpyrazole derivatives of general formula IV within a container for the aforesaid derivative or derivatives of general formula IV, or a said herbicidal composition, and instructions physically associated with the aforesaid container setting out the manner in which the aforesaid derivative or derivatives of general formula IV or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular, herbicidal compositions, boxes, for example of cardboard, plastics materials and metal, or sacks. The containers will normally be of sufficient capacity to contain amounts of the N-phenylpyrazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 10 kg of active material per hectare in the manner and for the purposes hereinbefore described.

The following Examples illustrate herbicidal compositions according to the present invention.

EXAMPLE 1

5-Amino-4-cyano-1-(2,6-dichloro-4-trifluoromethylphenyl)pyrazole was formulated as a water soluble concentrate containing 5-amino-4-cyano-1-(2,6-dichloro-4-trifluoromethylphenyl)-pyrazole: 10% w/v (weight/volume)

Ethylan KEO (nonylphenyl/ethylene oxide condensate containing 9–10 moles of ethylene oxide per mol of phenol): 10% w/v Dimethylformamide to 100% by volume, by dissolving the Ethylan KEO in a portion of dimethylformamide and then adding the active ingredient with heating and stirring until dissolved. The resulting solution was then made up to 100% by volume by adding the rest of the dimethylformamide.

5 Liters of the above formulation may be dissolved in 200 liters of water and sprayed post-emergence onto 1 hectare of an emerged crop of spring-sown wheat to control *Amaranthus retroflexus, Setaria viridis, Polygonum lapathifolium, Abutilon theophrasti* and *Solanum nigrum.*

The 5-amino-4-cyano-1-(2,6-dichloro-4-trifluoromethylphenyl)pyrazole may, if desired, be replaced in the above water soluble concentrate by any other compound of general formula IV.

EXAMPLE 2

A wettable powder was formed from:

5-amino-4-cyano-1-(2,6-dichloro-4-trifluoromethylphenyl)pyrazole: 50% w/w (weight/weight)

Ethylan BCP (a nonylphenol/ethylene oxide condensate containing 9 moles of ethylene oxide per mol of phenol): 5% w/w Aerosil (silicon dioxide of microfine particle size): 5% w/w Celite PF (synthetic magnesium silicate carrier): 40% w/w by adsorbing the Ethylan BCP onto the Aerosil, mixing with the other ingredients and grinding the mixture in a hammermill to give a wettable powder which may be diluted with water and applied at an application rate of 1.0 kg of wettable powder in 300 liters of spray fluid per hectare to control the growth of *Galium aparine, Veronica persica, Viola arvensis, Galeopsis tetrahit* and *Stellaria media* by post-emergence application in an emerged crop of winter wheat.

Similar wettable powders may be prepared as described above by replacing the 5-amino-4-cyano-1-(2,6-dichloro-4-trifluoromethylphenyl)pyrazole by other compounds of general formula IV.

EXAMPLE 3

An aqueous suspension concentrate was formed from:

5-amino-4-cyano-1-(2,6-dichloro-4-trifluoromethylphenyl)pyrazole: 50% w/v

Ethylan BCP: 1.0% w/v

Sopropon T36 (sodium salt of polycarboxylic acid): 0.2% w/v

Ethylene glycol: 5% w/v

Rhodigel 23 (polysaccharide xanthan gum thickener): 0.15% w/v distilled water to 100% by volume by intimately mixing the ingredients and grinding in a ball-mill for 24 hours. The concentrate thus obtained may be dispersed in water and applied at an application rate of 1.0 kg of aqueous suspension concentrate in 300 liters of spray fluid per hectare to control the growth of *Galium aparine, Veronica persica, Viola arvensis, Stellaria media* and *Galeopsis tetrahit* by post-emergence application in an emerged crop of winter barley.

Similar aqueous suspension concentrates may be prepared as described above by replacing the 5-amino-4-cyano-1-(2,6-dichloro-4-trifluoromethylphenyl)-pyrazole by other compounds of general formula IV.

EXAMPLE 4

An emulsifiable suspension concentrate was formed from:

5-amino-4-cyano-1-(2-chloro-4-trifluoromethylphenyl)-pyrazole: 50% w/v

Ethylan TU (a nonyl phenol/ethylene oxide condensate containing 10 moles of ethylene oxide per mol of phenol): 10% w/v Bentone 38 (an organic derivative of special magnesium montmorillonite thickener): 0.5% w/v Aromasol H (an aromatic solvent consisting predominantly of isomeric trimethylbenzenes: to 100% by volume by intimately mixing the ingredients and grinding in a ball-mill for 24 hours. The emulsifiable suspension concentrate thus obtained may be diluted with water and applied at an application rate of 2.0 kg of emulsifiable suspension concentrate in 100 liters of spray fluid per hectare to control the growth of *Setaria viridis, Polygonum convolvulus,* and *Chenopodium album* by post-emergence application in an emerged crop of spring-sown wheat.

Similar emulsifiable suspension concentrates may be prepared as described above by replacing the 5-amino-4-cyano-1-(2-chloro-4-trifluoromethylphenyl)pyrazole by other compounds of general formula IV.

EXAMPLE 5

Granules were formed from:

5-amino-4-cyano-1-(2,6-dichloro-4-trifluoromethylphenyl)pyrazole: 5% w/w

Ethylan BCP: 1% w/w

Oleic acid: 1% w/w

Aromasol H: 12% w/w

30/60 Attapulgite granules (sorptive silica clay): 81% w/w by mixing the phenylpyrazole, Ethylan BCP, oleic acid and Aromasol H and spraying the mixture onto the Attapulgite granules. The granules thus obtained may be applied at an application rate of 20 kg of granules per hectare to control the growth of *Echinochloa crus-galli, Eleocharis acicularis* and *Monochoria vaginalis* by pre-emergence application or application to seedling weeds in a crop of transplanted paddy rice.

Similar granules may be prepared as described above by replacing the 5-amino-4-cyano-1-(2,6-dichloro-4-trifluoromethylphenyl)pyrazole by other compounds of general formula IV.

EXAMPLE 6

A water soluble concentrate was formed from:
5-amino-4-cyano-1-(2,6-dichloro-4-trifluoromethylphenyl)pyrazole: 10% w/v
Ethylan KEO: 10% w/v
Dimethylformamide: to 100% by volume by dissolving the Ethylan KEO in a portion of dimethylformamide and then adding the pyrazole derivative with heating and stirring until dissolved. The resulting solution was then made up to 100% by volume with dimethylformamide by adding the rest of the dimethylformamide. The water soluble concentrate thus obtained may be diluted with water and applied at an application rate of 10 liters of water soluble concentrate in 200 to 2000 liters of spray fluid per hectare to control the growth of *Galium aparine, Veronica persica, Viola arvensis* and *Galeopsis tetrahit* by post-emergence application in an emerged crop of winter wheat at the tillering growth stage.

EXAMPLE 7

A wettable powder was formed from:
5-amino-4-cyano-1-(2,6-dichloro-4-trifluoromethylphenyl)pyrazole: 90% w/w
Arylan S (sodium dodecyl benzene sulphonate): 2% w/w
Darvan No. 2 (sodium lignosulphate): 5% w/w
Celite PF: 3% w/w
by mixing the ingredients and grinding the mixture in a hammer-mill to give a wettable powder which may be diluted with water and applied at an application rate of 1.0 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

Similar wettable powders may be prepared as described above by replacing the 5-amino-4-cyano-1-(2,6-dichloro-4-trifluoromethylphenyl)pyrazole by other compounds of general formula IV.

EXAMPLE 8

A wettable powder containing 50% w/w of 5-amino-4-cyano-1-(2,6-dichloro-4-trifluoromethylphenyl)-pyrazole, prepared as hereinbefore described in Example 2, may be diluted with water and applied at an application rate of 0.1 kg of wettable powder in 300 liters of spray fluid per hectare to control the growth of *Abutilon theophrasti* and *Polygonum convolvulus* by post-emergence application at the early seedling growth stage of these weeds in a crop of spring wheat.

EXAMPLE 9

A wettable powder containing 50% w/w of 5-amino-4-cyano-1-(2,6-dichloro-4-trifluoromethylphenyl)-pyrazole, prepared as described in Example 2, may be diluted with water and applied at an application rate of 20 kg of wettable powder in 600 liters of spray fluid per hectare to produce a total herbicidal effect on vegetation at a locus which is not a crop-growing area.

EXAMPLE 10

An emulsifiable concentrate was formed from:
5-amino-4-cyano-1-(2,3,5,6-tetrafluoro-4-trifluoromethylphenyl)pyrazole: 20% w/v
Soprophor BSU (condensate of tristyrylphenol and ethylene oxide, containing 18 moles of ethylene oxide): 3.75 w/v
Arylan CA (70% solution of calcium dodecyl benzene sulphonate): 3.75 w/v
Isophorone: 60% w/v Aromasol H: to 100% by volume,
by dissolving the Soprophor BSU and Arylan CA in a portion of the isophorone and then adding the phenylpyrazole, with heating, and stirring until dissolved. The remaining isophorone was then added and the solution was made up to 100% by volume by adding the Aromasol H. The emulsifiable concentrate thus obtained may be diluted with water and applied at an application rate of 1 liter of emulsifiable concentrate in 200 liters of spray fluid per acre to control the growth of *Galium aparine, Stellaria media, Veronica persica, Veronica hederifolia* and *Viola arvensis* by post-emergence application in an emerged crop of winter wheat.

EXAMPLE 11

An aqueous suspension concentrate containing 50% w/v of 5-amino-4-cyano-1-(2,6-dichloro-4-trifluoromethylphenyl)-pyrazole prepared as described in Example 3 (1.25 liters) and a commercially available 50% w/v aqueous suspension concentrate of isoproturon (15 liters) were mixed with water in the spray tank and applied at an application rate of 0.125 kg of the N-phenylpyrazole derivative and 1.5 kg of isoproturon in 200 liters of spray fluid per hectare to an emerged crop of winter wheat to control the growth of *Alopecurus myosuroides, Stellaria media, Matricaria inodora, Gallium aparine, Veronica persica* and *Viola arvensis* by post-emergence application.

According to a feature of the present invention, the N-phenylpyrazole derivatives of general formula IV wherein $R^{12}$, $R^{13}$, $R^{14}$ and $R^{15}$ are as hereinbefore defined, are prepared by the process which comprises the cyclisation of a compound of the general formula:

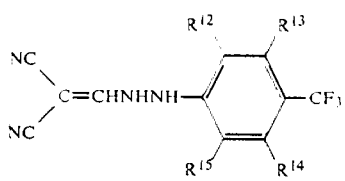

wherein the various symbols are as hereinbefore defined. Cyclisation may be effected in the presence of an inert organic solvent, for example an alkanol containing from 1 to 4 carbon atoms (e.g. ethanol), acetic acid or ethoxyethanol, at a temperature of from ambient temperature up to the reflux temperature of the reaction mixture.

Compounds of general formula V may be prepared by the reaction of a compound of the general formula:

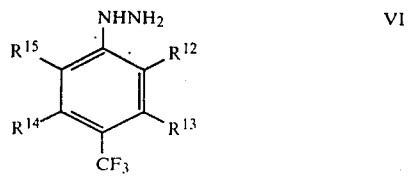

(wherein the various symbols are as hereinbefore defined) or an acid addition salt thereof (e.g. the hydrochloride) with a compound of the general formula:

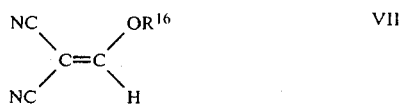

wherein $R^{16}$ represents a straight- or branched-chain alkyl radical containing from 1 to 4 carbon atoms, preferably ethyl.

The reaction of a compound of general formula VI with a compound of general formula VII may be effected in the presence of an inert organic solvent, for example an alkanol containing from 1 to 4 carbon atoms (e.g. ethanol), acetic acid or ethoxyethanol and at a temperature of from ambient temperature to the reflux temperature of the reaction mixture and optionally in the presence of an alkali metal (e.g. sodium or potassium) acetate, carbonate or bicarbonate. When an acid addition salt of the compound of general formula VI is used, the reaction with the compound of general formula VII is effected in the presence of an alkali metal (e.g. sodium or potassium) acetate, carbonate or bicarbonate.

N-Phenylpyrazole derivatives of general formula IV wherein $R^{12}$, $R^{13}$, $R^{14}$ and $R^{15}$ are as hereinbefore defined, may, according to another feature of the present invention, be prepared by reaction of a compound of general formula VI with a compound of general formula VII as hereinbefore described without isolation of an intermediate compound of general formula V from the reaction mixture. When the reaction of a compound of general formula VI with a compound of general formula VII is effected in acetic acid, in the absence or presence of an alkali metal (e.g. sodium or potassium) acetate, the intermediate compound of formula V may separate from the reaction mixture, depending upon the solubility of the intermediate compound of general formula V in the reaction medium, and may, if desired, be isolated before being cyclised as hereinbefore described to a compound of general formula IV, preferably by heating in an inert organic solvent (e.g. ethoxyethanol) at the reflux temperature of the reaction mixture.

Isolated compounds of general formula V exhibit herbicidal activities similar to those of the corresponding N-phenylpyrazole derivatives of general formula IV into which they may be cyclised, and it is believed that the herbicidal activity of compounds of general formula V results from their cyclisation to compounds of general formula IV.

Compounds of general formula VI and VII may be prepared by methods known per se. By the term "methods known per se" as used in the present specification is meant methods heretofore used or described in the chemical literature.

The following Examples and Reference Examples illustrate the preparation of compounds of general formula IV.

EXAMPLE 12

Ethoxmethylenemalononitrile [1.84 g; described by Huber, J. Amer. Chem. Soc., 65, 2224 (1943)] and 2,6-dichloro-4-trifluoromethylphenylhydrazine (3.7 g) were added to a magnetically-stirred solution of sodium acetate (0.6 g) in glacial acetic acid (15 ml) at laboratory temperature. After stirring for 15 minutes, a colourless solid precipitated from the clear brown solution obtained and stirring was continued for a further 15 minutes. The mixture was then filtered. The solid obtained was washed successively with acetic acid, water, aqueous sodium bicarbonate solution and water, to give 2,6-dichloro-4-trifluoromethylphenylhydrazinomethylenemalononitrile (3.4 g), m.p. 153°–154° C., in the form of colourless crystals.

The 2,6-dichloro-4-trifluoromethylphenylhydrazinomethylenemalononitrile thus obtained was then heated at reflux for 45 minutes in ethoxyethanol (15 ml). The hot solution was filtered and the filtrate was cooled, diluted with water (5 ml), and filtered, to give 5-amino-4-cyano-1-(2,6-dichloro-4-trifluoromethylphenyl)pyrazole (2.5 g), m.p. 165°–167° C., in the form of off-white crystals.

By proceeding in a similar manner, but replacing the 2,6-dichloro-4-trifluoromethylphenylhydrazine by the hereinafter indicated appropriately substituted phenylhydrazine, there were prepared:

5-Amino-1-(2-chloro-4-trifluoromethylphenyl)-4-cyanopyrazole, m.p. 185°–187° C., after crystallisation from toluene, in the form of fawn-coloured crystals, from 2-chloro-4-trifluoromethylphenylhydrazine, via 2-chloro-4-trifluoromethylphenylhydrazinomethylenemalononitrile, in the form of a brown powder, m.p. 138°–143° C.

5-Amino-4-cyano-1-(2,3,5,6-tetrafluoro-4-trifluoromethylphenyl)pyrazole, m.p. 122°–122.5° C., after crystallisation from toluene, in the form of off-white crystals, from 2,3,5,6-tetrafluoro-4-trifluoromethylphenylhydrazine (prepared as described by Alsop et al, J. Chem. Soc. 1962, 1801), via 2,3,5,6-tetrafluorophenyl-4-trifluoromethylphenylhydrazinomethylenemalononitrile, m.p. 90°–93° C., in the form of a pale yellow solid.

EXAMPLE 13

2,3,6-Trichloro-4-trifluoromethylphenylhydrazine (10.1 g) was added in one portion to a solution of ethoxymethylenemalononitrile (4.40 g) and anhydrous sodium acetate (1.47 g) in glacial acetic acid (34 ml) stirred at laboratory temperature. After stirring at laboratory temperature for 5 minutes, a fine precipitate formed and stirring at laboratory temperature was continued for 2 hours. The reaction mixture was then allowed to stand overnight at laboratory temperature and filtered. The solid precipitate was washed successively with a small quantity of glacial acetic acid, saturated aqueous sodium bicarbonate solution and water, to give 2,3,6-trichloro-4-trifluoromethylphenylhydrazinomethylenemalononitrile (9.6 g), m.p. 169°–170° C., in the form of a fawn-coloured powder.

The 2,3,6-trichloro-4-trifluoromethylphenylhydrazinomethylenemalononitrile thus obtained was heated at reflux for 1 hour in ethoxyethanol (50 ml). The hot solution was filtered and the filtrate was cooled, diluted with water (70 ml) and the solid precipitate was filtered off to give 5-amino-4-cyano-1-(2,3,6-trichloro-4-trifluoromethylphenyl)-pyrazole (6.36 g), m.p. 186°–187° C., after crystallisation from toluene (25 ml), in the form of a buff-coloured crystalline solid.

REFERENCE EXAMPLE 1

Phenylhydrazines used as starting materials in Examples 12 and 13 were prepared as follows:

2,6-Dichloro-4-trifluoromethylphenylaniline (4.3 g) (described in U.S. Pat. No. 3850955) was dissolved, with stirring, in glacial acetic acid (23 ml). A solution of sodium nitrite (1.5 g) in concentrated sulphuric acid (11 ml) was then added at 55°–60° C. The solution thus obtained was cooled to 0°–5° C. and a solution of stannous chloride (16.4 g) in concentrated hydrochloric acid (14 ml) was added with vigorous stirring. A cream-coloured solid precipitated. The mixture was filtered and the solid obtained was added to a mixture of aqueous ammonium hydroxide solution and ice. The mixture thus obtained was extracted with diethyl ether (6×500 ml) and the combined ethereal extracts were dried over sodium sulphate, filtered and evaporated to dryness to give 2,6-dichloro-4-trifluoromethylphenylhydrazine (3.7 g), m.p. 54°–56° C., in the form of a colourless crystalline solid.

By proceeding in a similar manner, but replacing the 2,6-dichloro-4-trifluoromethylaniline by 2-chloro-4-trifluoromethylaniline (described in U.S. Pat. No. 3850955), there was prepared 2-chloro-4-trifluoromethylphenylhydrazine, m.p. 38°–39° C., in the form of a colourless solid.

By proceeding in a similar manner, but replacing the 2,6-dichloro-4-trifluoromethylaniline by 2,3,6-trichloro-4-trifluoromethylaniline, there was prepared 2,3,6-trichloro-4-trifluoromethylphenylhydrazine, m.p. 72°–74° C., in the form of a white solid.

REFERENCE EXAMPLE 2

2,3,6-Trichloro-4-trifluoromethylaniline, used as a starting material in Reference Example 1, was prepared as follows:

A mixture of 3-chloro-4-trifluoromethylaniline [20 g; described in British patent specification No. 459890] and hydrochloric acid (d:1.18; 12 ml) was suspended in water (600 ml). Chlorine gas (from 13 ml of liquid chlorine) was then passed into the stirred suspension with heating at reflux. On completion of the addition of chlorine gas, stirring was continued for a further 15 minutes. After cooling, the solution thus obtained was extracted with dichloromethane (3×250 ml). The combined organic extracts were washed with water, saturated aqueous sodium bicarbonate solution and water, dried over anhydrous sodium sulphate and evaporated. The red oil thus obtained was distilled (bp 143°–147° C./20 mmHg) to give an orange oil which crystallized on standing to give 2,3,6-trichloro-4-trifluoromethylaniline (12.26 g), m.p. 37°–39° C., in the form of an orange solid.

We claim:
1. An N-phenylpyrazole derivative of the formula:

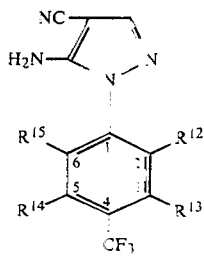

where $R^{12}$ represents a chlorine atom and $R^{13}$, $R^{14}$ and $R^{15}$ each represent a hydrogen atom, or $R^{12}$ and $R^{15}$ each represent a chlorine atom and $R^{13}$ and $R^{14}$ each represent a hydrogen atom, or $R^{12}$, $R^{13}$ and $R^{15}$ each represent a chlorine atom and $R^{14}$ represents a hydrogen atom, or $R^{12}$, $R^{13}$, $R^{14}$ and $R^{15}$ each represent a fluorine atom.

2. An N-phenylpyrazole derivative according to claim 1, which is 5-amino-1-(2-chloro-4-trifluoromethylphenyl)-4-cyanopyrazole.

3. An N-phenylpyrazole derivative according to claim 1, which is 5-amino-4-cyano-1-(2,6-dichloro-4-trifluoromethylphenyl)pyrazole.

4. An N-phenylpyrazole derivative according to claim 1, which is 5-amino-4-cyano-1-(2,3,6-trichloro-4-trifluoromethylphenyl)pyrazole.

5. An N-phenylpyrazole derivative according to claim 1, which is 5-amino-4-cyano-1-(2,3,5,6-tetrafluoro-4-trifluoromethylphenyl)pyrazole.

6. A herbicidal composition which comprises, as active ingredient, a herbicidally effective amount of an N-phenylpyrazole derivative of the general formula:

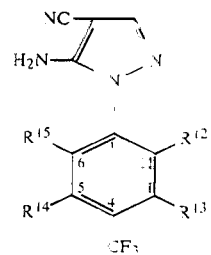

where $R^{12}$ represents a chlorine atom and $R^{13}$, $R^{14}$ and $R^{15}$ each represent a hydrogen atom, or $R^{12}$ and $R^{15}$ each represent a chlorine atom and $R^{13}$ and $R^{14}$ each represent a hydrogen atom, or $R^{12}$, $R^{13}$ and $R^{15}$ each represent a chlorine atom and $R^{14}$ represents a hydrogen atom, or $R^{12}$, $R^{13}$, $R^{14}$ and $R^{15}$ each represent a fluorine atom, in association with one or more compatible herbicidally-acceptable diluents or carriers.

7. A herbicidal composition according to claim 6, which contains from 0.05 to 90% by weight of N-phenylpyrazole derivative.

8. A herbicidal composition according to claim 6 or 7, which contains from 0.05 to 25% of surface-active agent.

9. A herbicidal composition according to claim 6 or 7, which contains from 0.05 to 10% of surface-active agent.

10. A herbicidal composition according to claim 6 or 7, which also contains isoproturon or chlortoluron.

11. A herbicidal composition according to claim 10, which contains isoproturon or chlortoluron in the ratio of 1:2.5 to 1:20 by weight of N-phenylpyrazole derivative to isoproturon or chlortoluron.

12. A herbicidal composition according to claim 6 or 7, in which the N-phenylpyrazole derivative incorporated in the composition is selected from the group consisting of 5-amino-1-(2-chloro-4-trifluoromethylphenyl)-4-cyanopyrazole, 5-amino-4-cyano-1-(2,6-dichloro-4-trifluoromethylphenyl)pyrazole and 5-amino-4-cyano-1-(2,3,5,6-tetrafluoro-4-trifluoromethylphenyl)pyrazole.

13. A herbicidal composition according to claim 6 or 7, in which the N-phenylpyrazole derivative incorporated in the composition is 5-amino-4-cyano-1-(2,3,6-trichloro-4-trifluoromethylphenyl)pyrazole.

14. A method of controlling the growth of weeds at a locus which comprises applying to the locus a herbicidally effective amount of an N-phenylpyrazole derivative of the general formula:

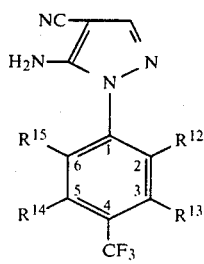

wherein $R^{12}$ represents a chlorine atom and $R^{13}$, $R^{14}$ and $R^{15}$ each represent a hydrogen atom, or $R^{12}$ and $R^{15}$ each represent a chlorine atom and $R^{13}$ and $R^{14}$ each represent a hydrogen atom, or $R^{12}$, $R^{13}$ and $R^{15}$ each represent a chlorine atom and $R^{14}$ represents a hydrogen atom, or $R^{12}$, $R^{13}$, $R^{14}$ and $R^{15}$ each represent a fluorine atom, in a herbicidal composition as claimed in claim 6 or 10.

15. A method according to claim 14, in which the weeds are broad-leafed weeds selected from *Abutilon theophrasti, Amaranthus retroflexus, Amsinckia intermedia, Anagallis arvensis, Atriplex patula, Brassica nigra, Capsella bursa-pastoris, Chenopodium album, Chrysanthemum segetum, Cirsium arvense, Datura stramonium, Desmodium tortuosum, Emex australis, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata, Polygonum* spp., (e.g., *Polygonum lapathifolium, Polygonum aviculare, Polygonum convolvulus* and *Polygonum persicaria*), *Portulaca oleracea, Raphanus raphanistrum, Rotala indicia, Rumex obtusifolius, Saponaria vaccaria, Scandix pectenveneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Canthium strumarium*.

16. A method according to claim 14, in which the weeds are grass weeds selected from *Alopecurus myosuroides, Apera spica-venti, Agrostis stolonifera, Avena fatua, Avena ludoviciana, Brachiaria* spp., *Bromus sterilis, Bromus tectorum, Cenchrus* spp., *Cynodon dactylon, Digitaria sanguinalis, Echinochloa crus-galli, Eleusine indica, Setaria viridis* and *Sorghum halepense* and sedges (e.g., *Cyperus esculentus, Cyperus iria* and *Cyperus rotundus*), and *Eleocharis acicularis*.

17. A method according to claim 15 or 16, wherein the N-phenylpyrazole derivative is applied pre- or post-emergence of the weeds.

18. A method according to claim 15 or 16, wherein the N-phenylpyrazole derivative is applied post-emergence of the weeds.

19. A method according to claim 14, in which the herbicidal composition is applied to an area used, or to be used, for growing crops.

20. A method according to claim 19, in which the herbicidal composition is applied to a crop-growing area at a rate sufficient to control the growth of weeds without causing substantial permanent damage to the crop.

21. A method according to claim 14 or 19, in which the N-phenylpyrazole derivative is applied at a rate between 0.01 kg and 10 kg per hectare.

22. A method according to claim 19 or 20, in which the crop is a cereal, soya beans, field or dwarf beans, peas, lucerne, cotton, peanuts, flax, onions, carrots, cabbage, oilseed rape, sunflower, sugar beet, or permanent or sown grassland.

23. A method according to claim 21, in which the crop is a cereal, soya beans, field or dwarf beans, peas, lucerne, cotton, peanuts, flax, onions, carrots, cabbage, oilseed rape, sunflower, sugar beet, or permanent or sown grassland.

24. A method according to claim 19, in which the crop is wheat, barley, oats, maize or rice.

25. A method according to claim 21, in which the crop is wheat, barley, oats, maize or rice.

26. A method according to claim 19 or 20, in which the N-phenylpyrazole derivative is applied at a rate between 0.05 kg and 4.0 kg per hectare.

27. A method according to claim 19 or 20, in which the N-phenylpyrazole derivative is applied at a rate between 0.1 kg and 2.0 kg per hectare.

28. A method according to claim 26, in which the herbicidal composition is applied for the control of broad-leafed weeds in an area used for growing a cereal crop before or after emergence of both the crop and weeds.

29. A method according to claim 27, in which the herbicidal composition is applied for the control of broad-leafed weeds in an area used for growing a cereal crop before or after emergence of both the crop weeds.

30. A method according to claim 28, in which the herbicidal composition is applied post-emergence of the broad-leafed weeds.

31. A method according to claim 29, in which the herbicidal composition is applied post-emergence of the broad-leafed weeds.

32. A method according to claim 24, in which the herbicidal composition is applied to an area containing an emerged cereal crop to control the growth of *Galium aparine, Veronica persica, Veronica hederifolia* or *Viola arvensis* by post-emergence application.

33. A method according to claim 25, in which the herbicidal composition is applied to an area containing an emerged cereal crop to control the growth of *Galium aparine, Veronica persica, Veronica hederifolia* or *Viola arvensis* by post-emergence application.

34. A method according to claim 26, in which the herbicidal composition is applied to an area containing an emerged cereal crop to control the growth of

*Galium aparine, Veronica persica, Veronica hederifolia* or *Viola arvensis* by post-emergence application.

35. A method according to claim 27, in which the herbicidal composition is applied to an area containing an emerged cereal crop to control the growth of *Galium aparine, Veronica persica, Veronica hederifolia* or *Viola arvensis* by post-emergence application.

36. A method according to claim 32, in which the cereal crop is wheat, barley or oats.

37. A method according to claim 14, in which a herbicidal composition which comprises, as active ingredient, an N-phenylpyrazole derivative of the general formula:

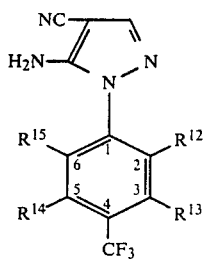

where $R^{12}$ represents a chlorine atom and $R^{13}$, $R^{14}$ and $R^{15}$ each represent a hydrogen atom, or $R^{12}$ and $R^{15}$ each represent a chlorine atom and $R^{13}$ and $R^{14}$ each represent a hydrogen atom, or $R^{12}$, $R^{13}$ and $R^{15}$ each represent a chlorine atom and $R^{14}$ represents a hydrogen atom, or $R^{12}$, $R^{13}$, $R^{14}$ and $R^{15}$ each represent a fluorine atom, and isoproturon or chlortoluron in association with one or more compatible herbicidally acceptable diluents or carriers is applied to control the growth of *Galium aparine, Veronica persica, Veronica hederifolia, Viola arvensis, Matricaria inodora, Stellaria media, Galeopsis tetrahit, Avena fatua* or *Alopecurus myosuroides* by post-emergence application.

38. A method according to claim 14, in which a herbicidal composition which comprises, as active ingredient, an N-phenylpyrazole derivative of the general formula:

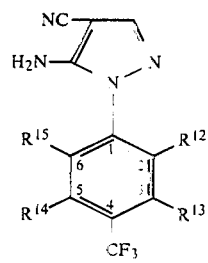

where $R^{12}$ represents a chlorine atom and $R^{13}$, $R^{14}$ and $R^{15}$ each represent a hydrogen atom, or $R^{12}$ and $R^{15}$ each represent a chlorine atom and $R^{13}$ and $R^{14}$ each represent a hydrogen atom, or $R^{12}$, $R^{13}$ and $R^{15}$ each represent a chlorine atom and $R^{14}$ represents a hydrogen atom or $R^{12}$, $R^{13}$, $R^{14}$ and $R^{15}$ each represent a fluorine atom, and isoproturon or chlortoluron in the ratio of 1:2.5 to 1:20 by weight of N-phenyl-pyrazole derivative to isoproturon or chlortoleuon in association with one or more compatible herbicidally acceptable diluents or carriers is applied to control the growth of *Galium aparine, Veronica persica, Veronica hederifolia, Viola arvensis, Matricaria inodora, Stellaria media, Galeopsis tetrahit, Avena fatua* or *Alopercurus myosuroides* by post-emergence application.

39. A method according to claim 37, in which the herbicidal composition is applied to an emerged crop of winter wheat or barley.

40. A method according to claim 38, in which the herbicidal composition is applied to an emerged crop of winter wheat or barley.

41. A method according to any one of claims 37 to 40, in which the N-phenylpyrazole derivative is applied at a rate of from 0.125 to 0.5 kg/ha and the isoproturon or chlortoluron is applied at a rate of from 1.25 to 2.5 kg/ha.

42. A method according to claim 14, in which the N-phenylpyrazole derivative applied to the locus is selected from the group consisting of 5-amino-1-(2-chloro-4-trifluoromethylphenyl)-4-cyanopyrazole, 5-amino-4-cyano-1-(2,6-dichloro-4-trifluoromethylphenyl)pyrazole, and 5-amino-4-cyano-1-(2,3,5,6-tetrafluoro-4-trifluoromethylphenyl)pyrazole.

43. A method according to claim 14, in which the N-phenylpyrazole derivative applied to the locus is 5-amino-4-cyano-1-(2,3,6-trichloro-4-trifluoromethylphenyl)pyrazole.

* * * * *

UNITED STATES PATENT AND TRADEMARK OFFICE
CERTIFICATE OF CORRECTION

PATENT NO. : 4,505,740
DATED : March 19, 1985
INVENTOR(S) : HATTON, et al.

It is certified that error appears in the above-identified patent and that said Letters Patent is hereby corrected as shown below:

On the title page:

In the heading after "[ ]" insert

--[30] Foreign Application Priority Data

July 17, 1981 [GB] United Kingdom ... 81 22142

February 5, 1982 [GB] United Kingdom ... 82 03369. --

Signed and Sealed this

Second Day of July 1985

[SEAL]

Attest:

DONALD J. QUIGG

*Attesting Officer*  *Acting Commissioner of Patents and Trademarks*